US009367818B2

(12) United States Patent
He et al.

(10) Patent No.: US 9,367,818 B2
(45) Date of Patent: *Jun. 14, 2016

(54) TRANSDUCTIVE LASSO FOR HIGH-DIMENSIONAL DATA REGRESSION PROBLEMS

(71) Applicant: International Business Machines Corporation, Armonk, NY (US)

(72) Inventors: Dan He, Ossining, NY (US); Laxmi P. Parida, Mohegan Lake, NY (US); Irina Rish, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 276 days.

This patent is subject to a terminal disclaimer.

(21) Appl. No.: 14/030,769

(22) Filed: Sep. 18, 2013

(65) Prior Publication Data

US 2014/0207714 A1    Jul. 24, 2014

Related U.S. Application Data

(63) Continuation of application No. 13/745,301, filed on Jan. 18, 2013.

(51) Int. Cl.
| | |
|---|---|
| *G06F 15/18* | (2006.01) |
| *G06N 99/00* | (2010.01) |
| *G06K 9/62* | (2006.01) |
| *G06F 17/18* | (2006.01) |
| *G06F 19/24* | (2011.01) |

(52) U.S. Cl.
CPC .............. *G06N 99/005* (2013.01); *G06F 17/18* (2013.01); *G06K 9/6247* (2013.01); *G06K 9/6256* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 6,789,070 B1 * | 9/2004 | Willett et al. | .................. 706/20 |
| 2012/0259807 A1 | 10/2012 | Dymetman | |
| 2012/0290521 A1 | 11/2012 | Frank et al. | |

OTHER PUBLICATIONS

"High-Dimensional Feature Selection by Feature-Wise Non-Linear Lasso" Yamada et al, Tokyo Institue of Technology Feb. 3, 2012.*
Non Final Office Action dated Jan. 7, 2015, received for U.S. Appl. No. 13/745,301.
Drineas, P., et al., "On the Nystrom Method for Approximating a Gram Matrix for Improved Kernel-Based Learning," Journal of Machine Learning Research, Dec. 2005, pp. 1-23, vol. 6.

(Continued)

*Primary Examiner* — Kakali Chaki
*Assistant Examiner* — Luis Sitiriche
(74) *Attorney, Agent, or Firm* — Fleit Gibbons Gutman Bongini & Bianco PL; Thomas Grzesik

(57) ABSTRACT

Various embodiments select features from a feature space. In one embodiment, a set of training samples and a set of test samples are received. A first centered Gram matrix of a given dimension is determined for each of a set of feature vectors that include at least one of the set of training samples and at least one of the set of test samples. A second centered Gram matrix of the given dimension is determined for a target value vector that includes target values from the set of training samples. A set of columns and rows associated with the at least one of the test samples in the second centered Gram matrix is set to 0. A subset of features is selected from a set of features based on the first and second centered Gram matrices.

12 Claims, 2 Drawing Sheets

(56) References Cited

OTHER PUBLICATIONS

Li, F., et al., "From Lasso Regression to Feature Vector Machine," Neutral Information Processing Systems, Dec. 2005, pp. 1-8.
Gammerman, A., et al. "Learning by Transduction", Proceedings of the Fourteenth Conference on Uncertainty in Artificial Intelligence, Jul. 1998, pp. 1-8.
Yang, Y., et al. "A Comparative Study on Feature Selection in Text Categorization" ICML '97 Proceedings of the Fourteenth International Conference on Machine Learning, Jul. 1997, pp. 1-9.
Alquier, P., "Lasso, Iterative Feature Selection and the Correlation Selector: Oracle inequalities and numerical performances", Electronic Journal of Statistics, Nov. 2008, pp. 1129-1152, vol. 2.
Dash, M., et al., "Feature Selection for Classification", Intelligent Data Analysis, Mar. 1997, pp. 131-156, vol. 1.
Guyon, I., et al., "An Introduction to Variable and Feature Selection", The Journal of Machine Learning Research 3, Mar. 2003, pp. 1157-1182.
Jain, A., et al., "Feature Selection: Evaluation, Application, and Small Sample Performance", IEEE Transactions on Pattern Analysis and Machine Intelligence, Feb. 1997, pp. 153-158, vol. 19, No. 2.
Tibshirani, R., "Regression Shrinkage and Selection via the Lasso", Journal of the Royal Statistical Society, Series B (Methodological), 1996, pp. 267-288, vol. 58, No. 1.
Yamada, M., et al.,"High-Dimensional Feature Selection by Feature-Wise Non-Linear Lasso", Feb. 2012, pp. 1-13.

\* cited by examiner

TRANSDUCTIVE LASSO FOR HIGH-DIMENSIONAL DATA REGRESSION PROBLEMS

CROSS-REFERENCE TO RELATED APPLICATIONS

This application is based upon and claims priority from prior U.S. patent application Ser. No. 13/745,301, filed on Jan. 18, 2013, now U.S. Pat. No. 9,135,567, the entire disclosure of which is herein incorporated by reference in its entirety.

BACKGROUND

The present invention generally relates to the field of feature selection, and more particularly relates to selecting features for linear regression.

Feature selection methods are critical for classification and regression problems. For example, it is common in large-scale learning applications, especially for biology data such as gene expression data and genotype data, that the amount of variables far exceeds the number of samples. The "curse of dimensionality" problem not only affects the computational efficiency of the learning algorithms, but also leads to poor performance of these algorithms. To address this problem, various feature selection methods can be utilized where a subset of important features is selected and the learning algorithms are trained on these features.

BRIEF SUMMARY

In one embodiment, a computer implemented method for selecting features from a feature space is disclosed. The method includes receiving, by a processor, a set of training samples and a set of test samples. Each of the set of training samples includes a set of features and a target value. The set of test samples includes the set of features absent the class value. A first centered Gram matrix of a given dimension is determined for each of a set of feature vectors that include at least one of the set of training samples and at least one of the set of test samples. A second centered Gram matrix of the given dimension is determined for a target value vector that includes the target values from the set of training samples. A set of columns and rows associated with the at least one of the test samples in the second centered Gram matrix is set to 0. A subset of features is selected from the set of features based on the first and second centered Gram matrices.

In another embodiment, an information processing system for selecting features from a feature space is disclosed. The information processing system includes a memory and a processor that is communicatively coupled to the memory. A feature selection module is communicatively coupled to the memory and the processor. The feature selection module is configured to perform a method. The method includes receiving a set of training samples and a set of test samples. Each of the set of training samples includes a set of features and a target value. The set of test samples includes the set of features absent the class value. A first centered Gram matrix of a given dimension is determined for each of a set of feature vectors that include at least one of the set of training samples and at least one of the set of test samples. A second centered Gram matrix of the given dimension is determined for a target value vector that includes the target values from the set of training samples. A set of columns and rows associated with the at least one of the test samples in the second centered Gram matrix is set to 0. A subset of features is selected from the set of features based on the first and second centered Gram matrices.

In a further embodiment, a non-transitory computer program product for selecting features from a feature space is disclosed. The non-transitory computer program product includes a storage medium readable by a processing circuit and storing instructions for execution by the processing circuit for performing a method. The method includes receiving a set of training samples and a set of test samples. Each of the set of training samples includes a set of features and a target value. The set of test samples includes the set of features absent the class value. A first centered Gram matrix of a given dimension is determined for each of a set of feature vectors that include at least one of the set of training samples and at least one of the set of test samples. A second centered Gram matrix of the given dimension is determined for a target value vector that includes the target values from the set of training samples. A set of columns and rows associated with the at least one of the test samples in the second centered Gram matrix is set to 0. A subset of features is selected from the set of features based on the first and second centered Gram matrices.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Figure 1:
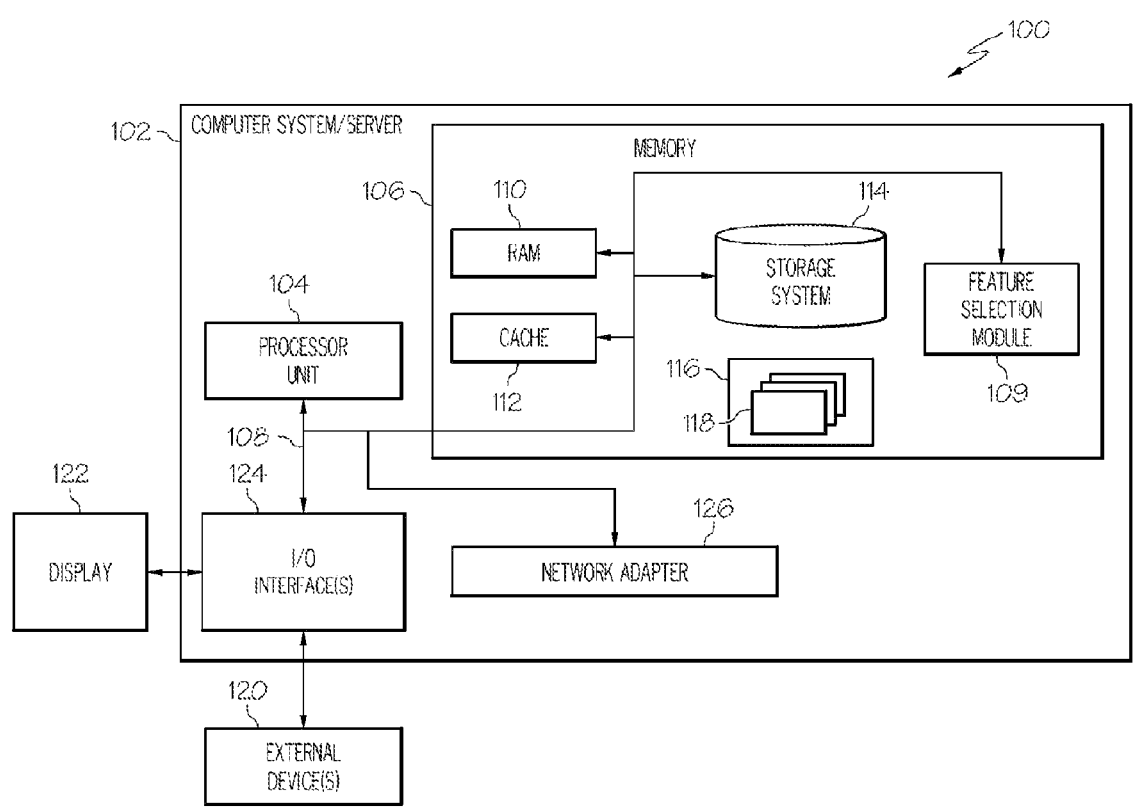
FIG. 1 is a block diagram illustrating one example of an operating environment according to one embodiment of the present invention.

FIG. 1 illustrates a general overview of one operating environment 100 according to one embodiment of the present invention. In particular, FIG. 1 illustrates an information processing system 102 that can be utilized in embodiments of the present invention. The information processing system 102 shown in FIG. 1 is only one example of a suitable system and is not intended to limit the scope of use or functionality of embodiments of the present invention described above. The information processing system 102 of FIG. 1 is capable of implementing and/or performing any of the functionality set forth above. Any suitably configured processing system can be used as the information processing system 102 in embodiments of the present invention.

As illustrated in FIG. 1, the information processing system 102 is in the form of a general-purpose computing device. The components of the information processing system 102 can include, but are not limited to, one or more processors or processing units 104, a system memory 106, and a bus 108 that couples various system components including the system memory 106 to the processor 104.

The bus 108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 106, in one embodiment, includes a feature selection module 109 configured to perform one or more embodiments discussed below. For example, in one embodiment, the feature selection 109 is configured to select features from a feature space based on a transductive Lasso (least absolute shrinkage and selection operator) feature selection mechanism, which is discussed in greater detail below. It should be noted that even though FIG. 1 shows the feature selection module 109 residing in the main memory, the feature selection module 109 can reside within the processor 104, be a separate hardware component capable of e, and/or be distributed across a plurality of information processing systems and/or processors.

The system memory 106 can also include computer system readable media in the form of volatile memory, such as random access memory (RAM) 110 and/or cache memory 112. The information processing system 102 can further include other removable/non-removable, volatile/non-volatile computer system storage media. By way of example only, a storage system 114 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. The memory 106 can include at least one program product having a set of program modules that are configured to carry out the functions of an embodiment of the present invention.

Program/utility 116, having a set of program modules 118, may be stored in memory 106 by way of example, and not limitation, as well as an operating system, one or more application programs, other program modules, and program data. Each of the operating system, one or more application programs, other program modules, and program data or some combination thereof, may include an implementation of a networking environment. Program modules 118 generally carry out the functions and/or methodologies of embodiments of the present invention.

The information processing system 102 can also communicate with one or more external devices 120 such as a keyboard, a pointing device, a display 122, etc.; one or more devices that enable a user to interact with the information processing system 102; and/or any devices (e.g., network card, modem, etc.) that enable computer system/server 102 to communicate with one or more other computing devices. Such communication can occur via I/O interfaces 124. Still yet, the information processing system 102 can communicate with one or more networks such as a local area network (LAN), a general wide area network (WAN), and/or a public network (e.g., the Internet) via network adapter 126. As depicted, the network adapter 126 communicates with the other components of information processing system 102 via the bus 108. Other hardware and/or software components can also be used in conjunction with the information processing system 102. Examples include, but are not limited to: microcode, device drivers, redundant processing units, external disk drive arrays, RAID systems, tape drives, and data archival storage systems.

The Lasso is a shrinkage and selection method for linear regression. Lasso minimizes the usual sum of squared errors for the purpose of regression, with the constraint that the L1-norm (the sum of the absolute values) of the parameter vector is no greater than a given value. Transduction assumes a setting where test data points are available to the learning algorithms. Therefore the learning algorithms can be more specific in that they can learn not only from the training data set, but also from the test data set. However, a challenge exists in determining how to utilize the test data points in the most useful way. For example, one usually only has access to the features of the test data points is, and not their class values. Therefore, it is generally difficult for one to integrate these features from the test data points into the learning algorithms. A general solution is imputation where the missing class values of the test data points are imputed by the model that is learned on the training data set only. Another type of imputation computes the missing class values of the test data points using their closest neighbors in the training data set. These imputation strategies, however, may not work well when the dimensionality of the data set is very high which usually leads to poor imputations. Therefore, it is very challenging to determine how to utilize the test data points in the most useful way.

One or more embodiments of the present invention provide a Transductive Lasso (TLASSO) shrinkage and selection mechanism. As will be discussed in greater detail below TLASSO is a feature-wise non-linear Lasso that utilizes a Hilbert-Schmidt independence criterion (HSIC). TLASSO not only utilizes considers training samples when selecting features from training samples, but also considers test samples as well.

As discussed above, Lasso refers to least absolute and utilizes linear dependency between input and output values to perform computationally efficient feature selection. EQ 1 below defines the Lasso optimization problem:

$$\min_{\alpha \in \mathbb{R}^d} \frac{1}{2}\|y - X \cdot \alpha\|_2^2 + \lambda \|\alpha\|_1, \tag{EQ 1}$$

where y is the target value, X* is the matrix of the features $\alpha = [\alpha_1, \ldots, \alpha_d]^*$ is a regression coefficient vector, $\alpha_k$ denotes the regression coefficient of the kth feature, $\|\cdot\|_1$ and $\|\cdot\|_2$ are the $l_1$ and $l_2$ norms, and $\lambda$ is the regularization parameter.

An HSIC Lasso is based on EQ 1 above and is defined as follows:

$$\min_{\alpha \in \mathbb{R}^d} \frac{1}{2}\left\|\bar{L}' - \sum_{k=1}^{d} \alpha_k \bar{K}'^{(k)}\right\|_{Frob}^2 + \lambda \|\alpha\|_1, \tag{EQ 2}$$

$$\text{s.t. } \alpha_1, \ldots, \alpha_d \geq 0,$$

where $\|\cdot\|_{Frob}$ is the Frobenius norm, $\bar{K}'^{(k)} = \Gamma K'^{(k)} \Gamma$ and $\bar{L}' = \Gamma L' \Gamma$ are centered Gram matrices, $K_{i,j}'^{(k)} = K'(x_{k,i}, x_{k,j})$ and $L'_{i,j} = L'(y_i, y_j)$ for $1 \leq i, j \leq n$ are Gram matrices, n is the number of samples, $K'(x,x')$ and $L'(y,y')$ are kernel functions, $$\Gamma = I_n - \frac{1}{n} 1_n 1_n^*$$

is the centering matrix, $I_n$ is the n-dimensional identity matrix, $1_n$ is the n-dimensional vector with all ones, and d is the total number of features. A more detail discussion on HSIC Lasso is given in Yamada et al., "High-Dimensional Feature Selection By Feature-Wise Non-Linear Lasso". Arxiv preprint arXiv:1202.0515, 2012, which is hereby incorporated by reference in its entirety.

It should be noted that in EQ 2 the non-negativity constraint is imposed and kernel functions K' and L' can be different. Also, the first term in EQ 2 indicates that the output kernel matrix $\bar{L}'$ is being regressed by a linear combination of feature-wise input kernel matrices $\{\bar{K}'^{(k)}\}_{k=1}^d$. It should be noted that since the output y of EQ 1 is transformed to the Gram matrix L in EQ 2 structured outputs can be incorporated via kernels.

The feature selection module 109, in one embodiment, takes as input a set of training samples, each containing a set of features and a target value. The feature selection module 109 also takes as input a set of test samples, each containing only the same set of features with target values missing. The number of features to be selected is also received by the feature selection module 109. In one embodiment, features can be represented as rows and samples as columns Therefore, the training and test samples include the same columns (features), but different rows (samples). Based on this input and the TLASSO feature selection mechanism defined by EQ 2 above and EQ 3 below, the feature selection module 109 outputs the missing target values of the test samples.

In one embodiment, the Frob normal of the HSIC Lasso defined in EQ 2 is extended into the following three components, where the last component is transductive:

$$\frac{1}{2}\left\|\bar{L}' - \sum_{k=1}^d \alpha_k \bar{K}'^{(k)}\right\|_{Frob}^2 = \quad \text{(EQ 3)}$$

$$\frac{1}{2}HSIC(y^{training}, y^{training}) - \sum_{k=1}^d \alpha_k HSIC(u_k^{training}, y^{training}) +$$

$$\frac{1}{2}\sum_{k,l=1}^d \alpha_k \alpha_l HSIC(u_k^{training+test}, u_l^{training+test}),$$

where $HSIC(u_k^{training}, y^{training}) = tr(\bar{K}'^{(k)}\bar{L})$ is a kernel based independence measure called the Hilbert-Schmidt independence criterion (HSIC), and $tr(\cdot)$ denotes the trace. HSIC $(y^{training}, y^{training})$ is a constant, and can be ignored.

The first component, $$\frac{1}{2}HSIC(y^{training}, y^{training}),$$

of EQ 3 relies only on target values $y^{training}$. The second component, $$\sum_{k=1}^d \alpha_k HSIC(u_k^{training}, y^{training}),$$

relies on both the target value, $y^{training}$ and the features $u_k^{training}$ considering the training samples. The third component, $$\frac{1}{2}\sum_{k,l=1}^d \alpha_k \alpha_l HSIC(u_k^{training+test}, u_l^{training+test}),$$

relies only on features, $u^{training+test}$ and $u_l^{training+test}$ but considers both the training samples and test samples.

The feature selection module 109 computes the centered Gram matrices for each feature column, which includes both the training and test samples. The centered Gram matrix of the target value column is computed using only the training samples. However, in order to match the dimensions of the matrices for the feature columns and for the target value column, the feature selection module 109 make the centered Gram matrix of the target value column to be of the same dimension as the matrix for the feature columns, as if target values for the test samples are available. Since target values for the test samples are not available, the feature selection module 109 sets the columns and rows in the centered Gram matrix for the target value column where the test samples are supposed to be involved as all 0.

The first component of EQ 3 is the trace of the product of the centered Gram matrix of the target value column to itself. Since the columns and rows in the matrix where the test samples are involved are set to 0 the trace remains unchanged from a trace where only the training samples are involved. The second component of EQ 3 is the trace of the product of the centered Gram matrix of the target value column to the centered Gram matrix of the feature columns Again, because the columns and rows in the matrix where the test samples are involved are set to 0 the trace remains unchanged from a trace where only the training samples are involved. The third component is the trace of the product of a pair of centered Gram matrices of the feature columns. The trace is computed using both the training and test samples and, therefore, is transductive. The feature selection module 109 then converts the TLasso of EQ 3 into a plain lasso problem by vectorizing the centered Gram matrices. This plain lasso problem can then be solved using exiting lasso solvers.

In one embodiment, the feature selection module 109 constructs $\bar{L}'$ and $\bar{K}'$ such that the left side and the right side of EQ 3 are equal, which allows Lasso solvers to solve the left side of the equation. In this embodiment, the feature selection module 109 applies a Gaussian kernel, where $$K'(x, x') = L'(x, x') = \exp\left(-\frac{(x-x')^2}{2\delta_x^2}\right)$$

and $\delta_x$=median $(|x_i - x_j|_{i,j=1}^n)$. Thus, for every feature vector, e.g., the feature vector of the k-th feature, the feature selection module 109 computes its corresponding Gram matrix $K'^{(k)}$. This Gram matrix $K'^{(k)}$ is determined by computing the Gaussian kernel function on every pair of vector elements, where the feature vectors include both the training and test samples. The centered Gram matrix of $\bar{K}'^{(k)}$ is then computed by multiplying the centering matrix $\Gamma$ on both sides of $K'^{(k)}$.

With respect to the target value vector, the feature selection module 109 computes its corresponding Gram matrix L', and then the centered Gram matrix $\bar{L}'$ in a similar manner However, the target values for the test samples are not available. Therefore, the feature selection module 109 constructs a target value vector where the first n values are the n values from the training samples, and the remaining n' values are set to infinity, where n' is the number of test samples. Then the feature selection module 109 first computes the Gram matrix L' using the kernel function, which is of size (n+n')×(n+n'). The feature selection module 109 sets the columns and rows with index [n+1, ..., n+n'] all to 0. The centered Gram matrix $\bar{L}'$ is computed by multiplying the centering matrix $\Gamma$ on both sides of L'. For each matrix multiplication, the feature selection module 109 sets the columns and rows with index [n+1, ..., n+n'] all to 0 in the resulting matrix.

The feature selection module 109 then vectorizes $\bar{L}'$ and $\bar{K}'^{(k)}$ for $1 \leq k \leq d$. For example, the feature selection module 109 concatenates the columns in the matrix into a single vector. After vectorization, for $\bar{L}'$ and each $\bar{K}'^{(k)}$, the feature selection module 109 obtains a vector of length (n+n')×(n+n'). Then for the d vectors from the d matrices $\bar{K}'^{(k)}$, the feature selection module 109 constructs a matrix where each of the d vectors is column, and the matrix is of size ((n+n')×(n+n'))×d. The two matrices from $\bar{L}'$ and $\bar{K}'^{(k)}$ can be inputted into one or more existing Lasso solvers, which outputs the coefficient of the selected features.

As an illustrative example, assume the input training dataset includes of 100 samples each including 5000 features and one target value. The input test dataset, in this example, includes 10 samples each including the same 5000 features. $\bar{L}'$ is a matrix of size 110×110, $\bar{K}'^{(k)}$ is a matrix of size 110×110, and there are $\bar{K}'^{(1)}, \bar{K}'^{(2)}, \ldots, \bar{K}'^{(5000)}$. To compute $\bar{K}'^{(k)}$, the feature selection module 109 uses both the 100 training samples and 10 test samples. To compute $\bar{L}'$, as the target values are not available for the test samples, the feature selection module 109 first computes $\bar{L}'$ using only the target values from the training samples, which is a matrix of size 100×100. Then the feature selection module sets the rows [101-110] and the columns [101-110] as 0 for the matrix $\bar{L}'$. Existing Lasso solvers can then be used to solve the left side of EQ 3.

Figure 2:
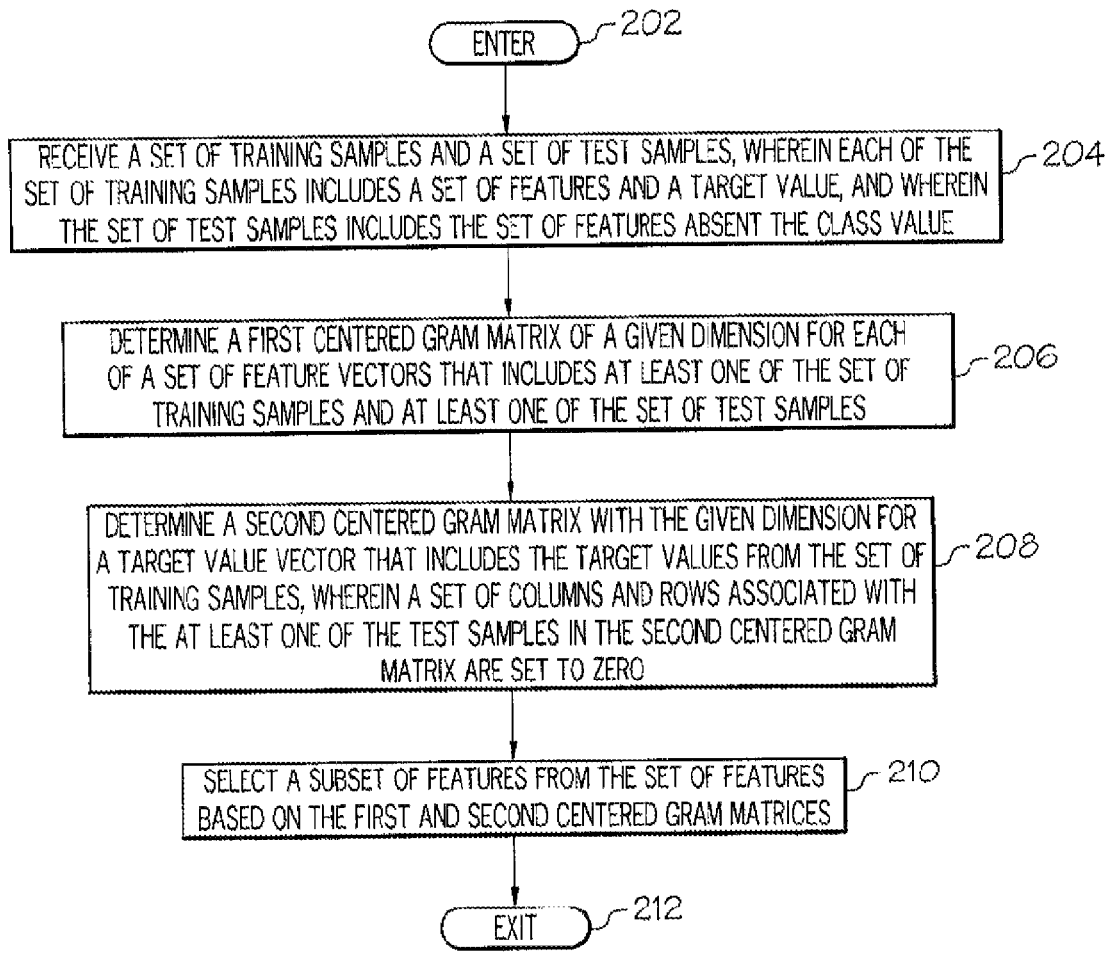
FIG. 2 is an operational flow diagram illustrating one example of a process for selecting features from a feature space based on a transductive Lasso (least absolute shrinkage and selection operator) feature selection mechanism according to one embodiment of the present invention.

FIG. 2 is an operational flow diagram illustrating one example of a process for selecting features from a feature space based on a transductive Lasso (least absolute shrinkage and selection operator) feature selection mechanism. The operational flow diagram begins at step 202 and flows directly to step 204. The feature selection module 109, at step 204, receives a set of training samples and a set of test samples. Each of the set of training samples includes a set of features and a target value. The set of test samples includes the set of features absent the class value. The feature selection module 109, at step 206, determines a first centered Gram matrix of a given dimension is determined for each of a set of feature vectors that include at least one of the set of training samples and at least one of the set of test samples. The feature selection module 109, at step 208, determines a second centered Gram matrix of the given dimension is determined for a target value vector that includes the target values from the set of training samples. A set of columns and rows associated with the at least one of the test samples in the second centered Gram matrix is set to 0. The feature selection module 109, at step 210, selects a subset of features from the set of features based on the first and second centered Gram matrices. The control flow exits at step 212.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems), and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An information processing system for selecting features from a feature space, the information processing system comprising:
    a memory;
    a processor communicatively coupled to the memory; and
    a feature selection module communicatively coupled to the memory and the processor, wherein the feature selection module programs the processor to perform a method comprising:
        receiving a set of training samples and a set of test samples, wherein each of the set of training samples comprises a set of features and a target value, and wherein the set of test samples comprises the set of features absent the target value;
        determining a first centered Gram matrix of a given dimension for each of a set of feature vectors comprising at least one of the set of training samples and at least one of the set of test samples;
        determining a second centered Gram matrix of the given dimension for a target value vector comprising the target values from the set of training samples, wherein a set of columns and rows associated with the at least one of the test samples in the second centered Gram matrix are set to 0;
        selecting a subset of features from the set of features based on the first and second centered Gram matrices; and
        presenting the subset of features that has been selected on a display.

2. The information processing system of claim 1, wherein determining each of the first centered Gram matrices comprises:
    determining, for each of the set of feature vectors, a Gram matrix based on computing, a Gaussian kernel function on each pair of vector elements in the feature vector; and
    multiplying a centering matrix on each side of the Gram matrix,
wherein determining the second centered Gram matrix comprises:
    generating the target value vector with a first n values being the target values from the set of training samples, and a remaining n' values being set to infinity, where n' is a number of test samples in the set of test samples;
    determining a Gram matrix based on computing, a Gaussian kernel function of size (n+n')×(n+n') on each pair of vector elements in the target value vector;
    setting a set of columns and rows in the Gram matrix with index [n+1, . . . , n+n'] to 0; and
    multiplying, after the setting, a centering matrix on each side of the Gram matrix.

3. The information processing system of claim 1, wherein the method further comprises:
    concatenating each column in the second centered Gram matrix into a vector of size (n+n')×(n+n'), where n corresponds to a number of target values in the set of training samples and n' corresponds to a number of test samples in the set of test samples.

4. The information processing system of claim 3, wherein the method further comprises:
    concatenating each column in each of the first centered Gram matrices into one of a set of d vectors of size (n+n')×(n+n'), where n corresponds to a number of target values in the set of training samples and n' corresponds to a number of test samples in the set of test samples; and
    generating a single matrix based on each of the set of d vectors, where each column of the single matrix is one of the set of d vectors, and where the single matrix is of a size (n+n')×(n+n')×d.

5. The information processing system of claim 4, wherein the subset of features are selected from the single matrix and the single vector.

6. The information processing system of claim 1, wherein the selecting is based on:

$$\min_{\alpha \in \mathbb{R}^d} \frac{1}{2} \left\| L' - \sum_{k=1}^{d} \alpha_k \overline{K}'^{(k)} \right\|^2_{Frob} + \lambda \|\alpha\|_1,$$

$$\text{s.t. } \alpha_1, \ldots, \alpha_d \geq 0,$$

where $$\frac{1}{2} \left\| L' - \sum_{k=1}^{d} \alpha_k \overline{K}'^{(k)} \right\|^2_{Frob} =$$

$$\frac{1}{2} HSIC(y^{training}, y^{training}) - \sum_{k=1}^{d} \alpha_k HSIC(u_k^{training}, y^{training}) +$$

$$\frac{1}{2} \sum_{k,l=1}^{d} \alpha_k \alpha_l HSIC(u_k^{training+test}, u_l^{training+test}),$$

and where $\|\cdot\|_{Frob}$ is a Frobenius norm, $\overline{K}^{(k)} = \Gamma K'^{(k)} \Gamma$ is the first centered Gram matrix, $\overline{L}' = \Gamma L' \Gamma$ is the second centered Gram matrix, $K'_{i,j}{}^{(k)} = K'(x_{k,i}, x_{k,j})$ and $L'_{i,j} = L'(y_i, y_j)$ for $1 \leq i, j \leq n$ are Gram matrices, n is the number of samples, $K'(x,x')$ and $L'(y,y')$ are kernel functions, $$\Gamma = I_n - \frac{1}{n} 1_n 1_n^*$$

is a centering matrix, $I_n$ is the n-dimensional identity matrix, $1_n$ is an n-dimensional vector with all ones, d is a total number of features, and HSIC is a Hilbert-Schmidt independence criterion.

7. A computer program product for selecting features from a feature space, the computer program product comprising:
   a non-transitory storage medium readable by a processing circuit and storing instructions for execution by the processing circuit, the instructions programming the processing circuit to perform a method comprising:
      receiving, by a processor, a set of training samples and a set of test samples, wherein each of the set of training samples comprises a set of features and a target value, and wherein the set of test samples comprises the set of features absent the target value;
      determining a first centered Gram matrix of a given dimension for each of a set of feature vectors comprising at least one of the set of training samples and at least one of the set of test samples;
      determining a second centered Gram matrix of the given dimension for a target value vector comprising the target values from the set of training samples, wherein a set of columns and rows associated with the at least one of the test samples in the second centered Gram matrix are set to 0;
      selecting a subset of features from the set of features based on the first and second centered Gram matrices; and
      presenting the subset of features that has been selected on a display.

8. The non-transitory computer program product of claim 7, wherein determining each of the first centered Gram matrices comprises:
   determining, for each of the set of feature vectors, a Gram matrix based on computing, a Gaussian kernel function on each pair of vector elements in the feature vector; and
   multiplying a centering matrix on each side of the Gram matrix, wherein determining the second centered Gram matrix comprises:
   generating the target value vector with a first n values being the target values from the set of training samples, and a remaining n' values being set to infinity, where n' is a number of test samples in the set of test samples;
   determining a Gram matrix based on computing, a Gaussian kernel function of size (n+n')×(n+n') on each pair of vector elements in the target value vector;
   setting a set of columns and rows in the Gram matrix with index [n+1, ..., n+n'] to 0; and
   multiplying, after the setting, a centering matrix on each side of the Gram matrix.

9. The non-transitory computer program product of claim 7, wherein the method further comprises:
   concatenating each column in the second centered Gram matrix into a vector of size (n+n')×(n+n'), where n corresponds to a number of target values in the set of training samples and n' corresponds to a number of test samples in the set of test samples.

10. The non-transitory computer program product of claim 9, wherein the method further comprises:
    concatenating each column in each of the first centered Gram matrices into one of a set of d vectors of size (n+n')×(n+n'), where n corresponds to a number of target values in the set of training samples and n' corresponds to a number of test samples in the set of test samples; and
    generating a single matrix based on each of the set of d vectors, where each column of the single matrix is one of the set of d vectors, and where the single matrix is of a size (n+d)×(n+n')×d.

11. The non-transitory computer program product of claim 10, wherein the subset of features are selected from the single matrix and the single vector.

12. The non-transitory computer program product of claim 7, wherein the selecting is based on:

$$\min_{\alpha \in \mathbb{R}^d} \frac{1}{2} \left\| \overline{L}' - \sum_{k=1}^{d} \alpha_k \overline{K}'^{(k)} \right\|_{Frob}^2 + \lambda \|\alpha\|_1,$$

$$\text{s.t.} \quad \alpha_1, \ldots, \alpha_d \geq 0,$$

where $$\frac{1}{2} \left\| \overline{L}' - \sum_{k=1}^{d} \alpha_k \overline{K}'^{(k)} \right\|_{Frob}^2 =$$

$$\frac{1}{2} HSIC(y^{training}, y^{training}) - \sum_{k=1}^{d} \alpha_k HSIC(u_k^{training}, y^{training}) +$$

$$\frac{1}{2} \sum_{k,l=1}^{d} \alpha_k \alpha_l HSIC(u_k^{training+test}, u_l^{training+test}),$$

and where $\|\cdot\|_{Frob}$ is a Frobenius norm, $\overline{K}^{(k)} = \Gamma K'^{(k)} \Gamma$ is the first centered Gram matrix, $\overline{L}' = \Gamma L' \Gamma$ is the second centered Gram matrix, $K'_{i,j}{}^{(k)} = K'(x_{k,i}, x_{k,j})$ and $L'_{i,j} = L'(y_i, y_j)$ for $1 \leq i, j \leq n$ are Gram matrices, n is the number of samples, $K'(x,x')$ and $L'(y,y')$ are kernel functions, $$\Gamma = I_n - \frac{1}{n} 1_n 1_n^*$$

is a centering matrix, $I_n$ is the n-dimensional identity matrix, $1_n$ is an n-dimensional vector with all ones, d is a total number of features, and HSIC is a Hilbert-Schmidt independence criterion.

* * * * *